United States Patent
Battefeld et al.

(10) Patent No.: US 9,638,626 B2
(45) Date of Patent: May 2, 2017

(54) NEPHELOMETRIC TURBIDIMETER VIAL ARRANGEMENT

(71) Applicant: HACH LANGE GMBH, Berlin (DE)

(72) Inventors: Manfred Battefeld, Duesseldorf (DE); Bas De Heij, Dormagen (DE); Hans-Joachim Kumpch, Berlin (DE); Andreas Mitreiter, Kleinmachnow (DE); Andreas Golitz, Moers (DE)

(73) Assignee: HACH LANGE GMBH, Berlin (DE)

( * ) Notice: Subject to any disclaimer, the term of this patent is extended or adjusted under 35 U.S.C. 154(b) by 0 days.

(21) Appl. No.: 14/951,505

(22) Filed: Nov. 25, 2015

(65) Prior Publication Data
US 2016/0153893 A1    Jun. 2, 2016

(30) Foreign Application Priority Data
Nov. 27, 2014 (EP) .................................... 14195060

(51) Int. Cl.
G01N 21/00    (2006.01)
G01N 21/15    (2006.01)
G01N 21/51    (2006.01)

(52) U.S. Cl.
CPC ............ *G01N 21/15* (2013.01); *G01N 21/51* (2013.01); *G01N 2021/513* (2013.01); *G01N 2201/0227* (2013.01); *G01N 2201/0642* (2013.01)

(58) Field of Classification Search
CPC ...... G01N 21/49; G01N 21/05; G01N 21/532; G01N 21/4785; G01N 21/53; G01N 21/15; G01N 21/0303; G01N 21/51; G01N 2021/513; G01N 2021/4726; G01N 2201/068

USPC ......... 356/432–440, 246; 422/512, 546, 550, 422/560

See application file for complete search history.

(56) References Cited

U.S. PATENT DOCUMENTS

| | | | |
|---|---|---|---|
| 5,872,361 A | 2/1999 | Paoli et al. | |
| 6,543,612 B2* | 4/2003 | Lee | B65D 81/3222 206/222 |
| 7,659,980 B1 | 2/2010 | Mitchell et al. | |
| 8,724,107 B2 | 5/2014 | Palumbo | |
| 2003/0214653 A1 | 11/2003 | Palumbo et al. | |
| 2007/0298487 A1* | 12/2007 | Bachur | B01L 3/545 435/287.2 |
| 2008/0149584 A1* | 6/2008 | Martinelli | B65B 7/285 215/201 |
| 2011/0128540 A1* | 6/2011 | Iida | G01J 1/04 356/319 |

OTHER PUBLICATIONS

Anonymous: "Wagner Glaswarenfabrik | vials | perfume sampler | flat bottom | perfume | essences", www.wagner-glaswarenfabrik.com, pp. 1-3 (May 5, 2015).

* cited by examiner

*Primary Examiner* — Hoa Pham
(74) *Attorney, Agent, or Firm* — Norman B. Thot (57) ABSTRACT

A nephelometric turbidimeter vial arrangement includes a vial and a separate vial cap. The vial comprises a transparent cylindrical vial body configured to enclose a vial interior, a bottom inlet window, and a top vial opening configured to be circular. The separate vial cap comprises a light trap cavity. The separate vial cap is configured to close the top vial opening. The light trap cavity comprises an inner surface which comprises a light absorbing surface. The light trap cavity is configured to be open to the vial interior.

20 Claims, 7 Drawing Sheets

NEPHELOMETRIC TURBIDIMETER VIAL ARRANGEMENT

CROSS REFERENCE TO PRIOR APPLICATIONS

Priority is claimed to European Patent Application No. 14,195,060.0, filed Nov. 27, 2014. The entire disclosure of said application is incorporated by reference herein.

FIELD

The present invention relates to a nephelometric turbidimeter vial arrangement for use in a nephelometric turbidimeter.

BACKGROUND

A nephelometric turbidimeter determines the concentration of solid particles or other particles suspended in a fluid which generally can be a liquid, a gas, or a mixture of liquid and gas. U.S. Pat. No. 8,724,107 B2 describes a nephelometric turbidimeter with a cylindrical turbidimeter vial comprising an optically transparent and flat bottom inlet window through which a measurement light beam axially enters the vial interior. A cylindrical section of the vial cylinder body defines a transparent outlet window through which the light scattered by the suspended particles radially exits the vial interior and is received by a light detecting means. The received primary light signal, which is caused only by the light scattered within the relevant fluid volume, is of relatively low intensity. Any light not caused by the light scattered within the relevant fluid volume but causing a secondary signal should therefore, if possible, be avoided.

The vial top opening is closed temporarily in case of a laboratory turbidimeter vial or is closed permanently in case of a process turbidimeter vial by a simple vial lid. If the turbidimeter vial is used to measure the turbidity of drinking water, the axial measurement light beam's intensity is reduced only minimally by the fluid turbidity so that the reflection of the measurement light beam at the vial lid's inside surface can cause a secondary light signal of high intensity which can be directly detected by the light detecting means. A secondary signal of high intensity could make it difficult, if not impossible, to determine the intensity of the primary light signal.

SUMMARY

An aspect of the present invention is to provide a nephelometric turbidimeter vial arrangement which avoids a strong secondary signal.

In an embodiment, the present invention provides a nephelometric turbidimeter vial arrangement which includes a vial and a separate vial cap. The vial comprises a transparent cylindrical vial body configured to enclose a vial interior, a bottom inlet window, and a top vial opening configured to be circular. The separate vial cap comprises a light trap cavity. The separate vial cap is configured to close the top vial opening. The light trap cavity comprises an inner surface which comprises a light absorbing surface. The light trap cavity is configured to be open to the vial interior.

BRIEF DESCRIPTION OF THE DRAWINGS

The present invention is described in greater detail below on the basis of embodiments and of the drawings in which.

DETAILED DESCRIPTION

The nephelometric turbidimeter is provided with a measurement light source generating a measurement light beam. The light source generates suitable electromagnetic radiation which can be of any suitable wavelength. The vial is situated in a vial chamber of the turbidimeter during the turbidity measurement. The measurement light beam is axially directed into the vial interior through a flat and plane bottom inlet window of the vial. The turbidimeter is also provided with a scattering light detecting arrangement to receive and detect the light scattered by particles suspended in the fluid sample in a substantially right angle with respect to the axial orientation of the measurement light beam.

The vial is can-shaped and is provided with a cylindrical transparent vial body which encloses the vial interior and which defines the circular vial top opening. The vial arrangement further comprises a separate vial cap which closes the vial opening at the vial's top. The proximal area of the vial cap is formed as a light trap cavity which is orientated to the vial interior. The inner surface of the light trap cavity is provided as a light absorbing surface and can, for example, be colored black. The light trap cavity is provided with a lateral side wall so that the light trap cavity has an axial cavity depth of at least some millimeters.

The light beam coming from the measurement light source impinges at the interior top structure of the light trap cavity and is thereby significantly absorbed by the light absorbing surface. The light fraction which is reflected by the top structure of the light trap cavity impinges at least partially at the lateral interior cavity side wall where the remaining light energy is significantly absorbed so that only a small fraction of the intensity of the measurement light beam entering the light trap cavity finally leaves the light trap cavity. The intensity of a secondary light signal which could finally be received by the light detecting arrangement is significantly reduced as a result.

In an embodiment of the present invention, the vial cap can, for example, be provided with an axial neck portion which extends into the vial interior and which defines at least a part of the light trap cavity. The vial neck portion has two functions. The vial neck portion firstly elongates the axial length of the light trap cavity so that the axial length of the light trap cavity can be greater than the axial length of the extending part of the vial cap which extends axially from the top vial opening. The axial neck portion secondly elongates the sealing length between the boundary surface between the vial cap and the vial body.

In an embodiment of the present invention, the radial outside of the axial neck portion can, for example, be provided with a circumferential sealing element. The sealing element can be provided as one or more circular sealing lips which axially extends from a cylindrical portion of the axial neck portion. The sealing element can also be provided as one single circumferential sealing bulge which defines an acute angle of less than 45° with the inner surface of the vial body at the contact zone, as seen in longitudinal cross-section. The circular sealing bulge has a high sealing quality and avoids the possibility that solid particles dissolved in the fluid sample are accumulated and thereby extracted from the sample fluid, which could then result in falsified turbidity measurement results.

In an embodiment of the present invention, the light trap cavity can, for example, be provided with a convex cone at the axial end of the light trap cavity. When the axial measurement light beam impinges at the convex cone, the measurement light beam is partially absorbed and is partially reflected laterally, but not axially. The laterally reflected fraction of the measurement light beam then completely impinges on the lateral side wall of the light trap cavity. As a result, the measurement light beam impinges at least twice at a light absorbing surface of the light trap cavity. This provides that only a small fraction of the measurement light beam is finally able to be reflected backwards into the vial interior. The intensity of a secondary light signal finally received by the light detecting arrangement can therefore be significantly reduced.

In an embodiment of the present invention, the vial cap can, for example, be provided with a chip cavity wherein a RFID chip is housed. The RFID chip can memorize information about the vial itself and/or about the fluid sample within the vial. The vial arrangement is generally manually held by a user in a vertical vial orientation so that the vial cap is at the top. This allows the user to easily position the vial cap close to a RFID reading device of the turbidimeter apparatus for starting and conducting a data transfer between the RFID chip and the RFID reading device.

In an embodiment of the present invention, the plane longitudinal chip cavity can, for example, be arranged in a substantially axial plane so that the vial cap's RFID chip including the RFID antenna is also arranged in a substantially axial plane. An axial plane is a plane which is substantially in parallel with the longitudinal axis of the cylindrical vial body. With the RFID chip being arranged in an axial plane, the predominant receiving and sending direction of the RFID antenna is substantially radial with respect to the longitudinal vial axis. If the RFID reading device of the turbidimeter is arranged with a horizontal predominant orientation, the electromagnetic coupling quality of the RFID reading device and the RFID chip is high.

In an embodiment of the present invention, the vial cap can, for example, be provided with a lateral grip recess. The grip recess motivates the user to grip the vial arrangement at the vial cap, but not at the vial body, so that fingerprints on the outside of the transparent vial body are avoided.

In an embodiment of the present invention, the vial cap can, for example, be provided with two grip recesses which are arranged opposed to each other. The grip recesses lie substantially in an axial plane opposed to each other so that the user is motivated to manually grip the vial cap with two fingers, for example, with the thumb and the index finger. The orientation of the chip plane of the RFID chip can, for example, be symmetric in the middle with respect to the orientations of the grip planes of the two grip recesses. If the grip recesses are arranged exactly opposite to each other, the basic plane of the RFID chip is arranged perpendicular with respect to both grip recess planes. When the user manually grips the vial cap with his fingers at the two grip recesses, the predominant electromagnetic orientation of the RFID chip and of the RFID antenna is substantially horizontal and in parallel with the fingers holding the vial cap. The user therefore intuitively moves the vial cap in direction of the predominant electromagnetic orientation of the RFID chip to the turbidimeter's RFID reading device. This arrangement is user-friendly and leads to a high reliability when using the RFID reading device of the turbidimeter.

In an embodiment of the present invention, a nephelometric turbidimeter vial cap can, for example, be provided with the cap-related features.

Two embodiments of the invention are described below with reference to the enclosed drawings.

FIGS. 1 to 8 show two embodiments of vial arrangements 8;8'. The vial arrangement 8 of the first embodiment shown in FIGS. 1 to 4 is provided with a more sophisticated light trap then vial arrangement 8' of the second embodiment shown in FIGS. 5 to 8. Both vial arrangements 8; 8' are provided with a basically cylindrical and can-like vial 10 with a top vial opening 13 which is closed by a separate vial cap 60;61. The vial body 14 is made out of light-transparent glass. The separate vial caps 60; 61 are made out of light-opaque and black-colored plastic.

Figure 1:
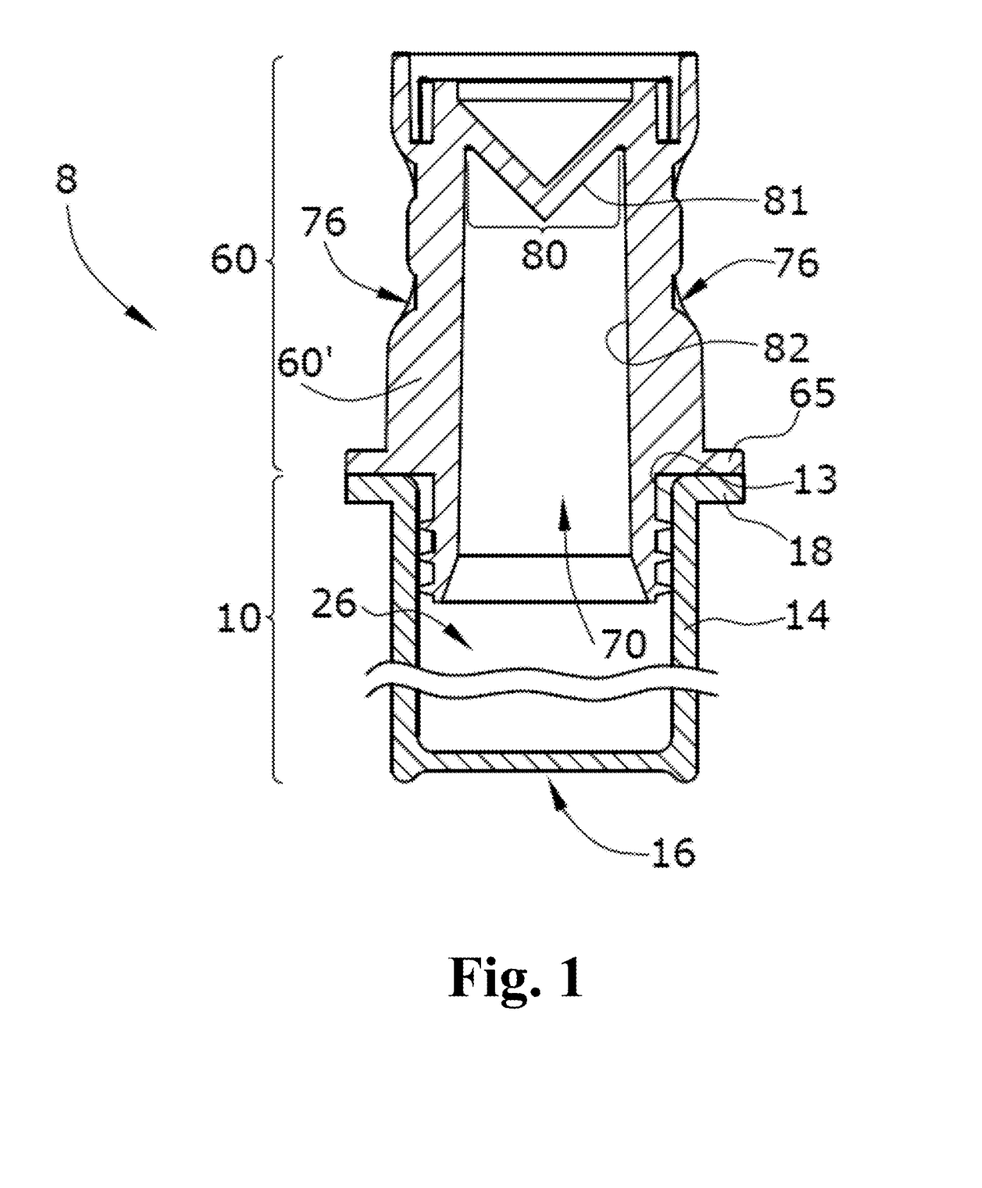
FIG. 1 shows a first longitudinal cross section of a first embodiment of a nephelometric turbidimeter vial arrangement in accordance with the present invention.
Figure 5:
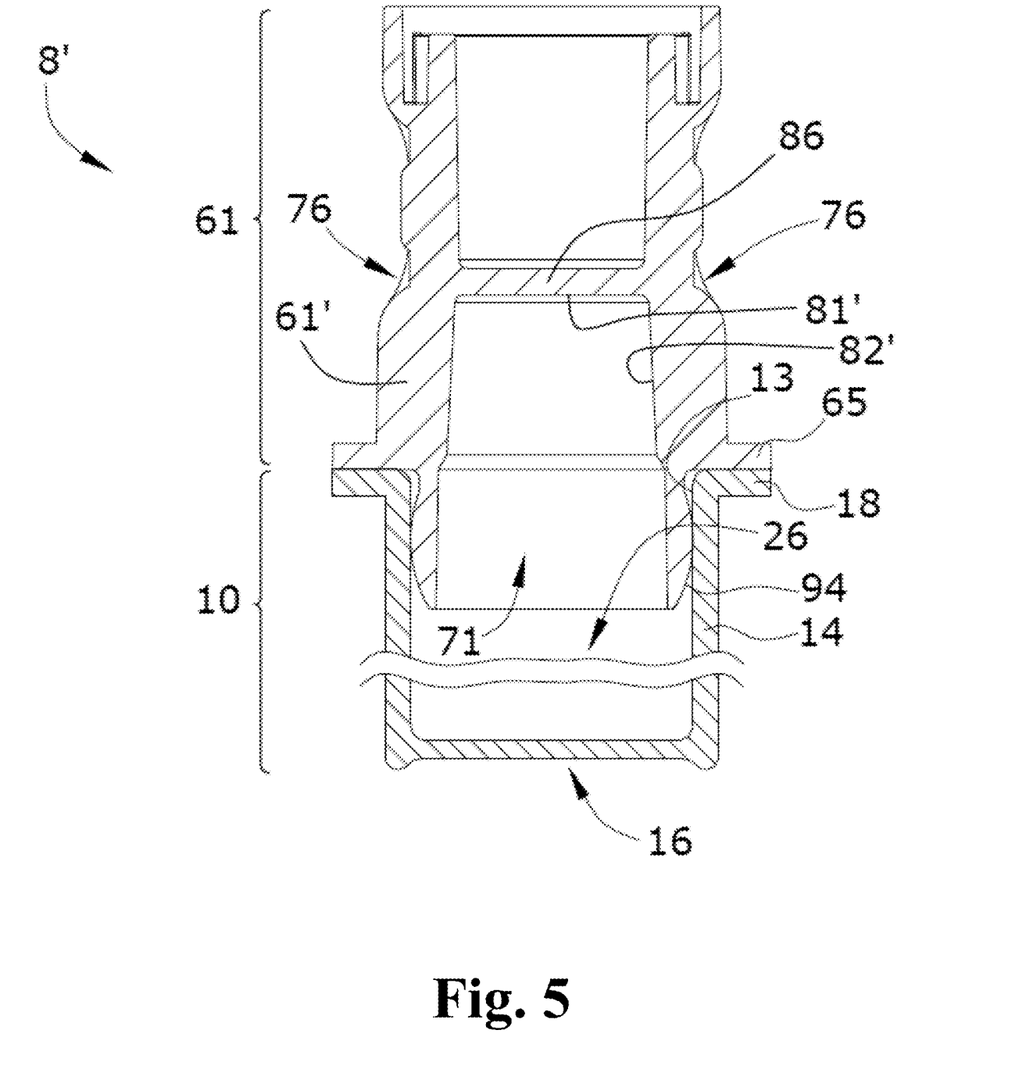
FIG. 5 shows a first longitudinal cross section of a second embodiment of a nephelometric turbidimeter vial arrangement in accordance with the present invention.

Both vial arrangements 8; 8' are adapted for use in a nephelometric turbidimeter which is provided with a measurement light source generating a measurement light beam which is directed axially into the vial interior through a transparent bottom light inlet window 16 of the vial 10. The light source generates a measurement light of a suitable wavelength and the light inlet window 16 is transparent for the measurement light. On the top end of the vial body 14, a top vial opening 13 is provided which is circular and which is surrounded by a radial vial flange 18. The vial body 14 encloses a vial interior 26. The vial 10 of both embodiments is identical, but the vial caps 60;61 are different from each other.

The vial cap 60 of the first embodiment of the vial arrangement 8 is made of a plastic cap body 60' of a black-colored plastic material. The vial cap body 60' is hollow and defines a longitudinal axial light trap cavity 70 in its interior. The light trap cavity 70 is provided with a slightly conical lateral surface 82 with a cone angle of less than 4°. The upper end of the light trap cavity 70 is provided with a convex cone 80 with a cone surface 81. The cone angle of the cone surface 81 is 90° and can alternatively be less than 90°.

Figure 2:
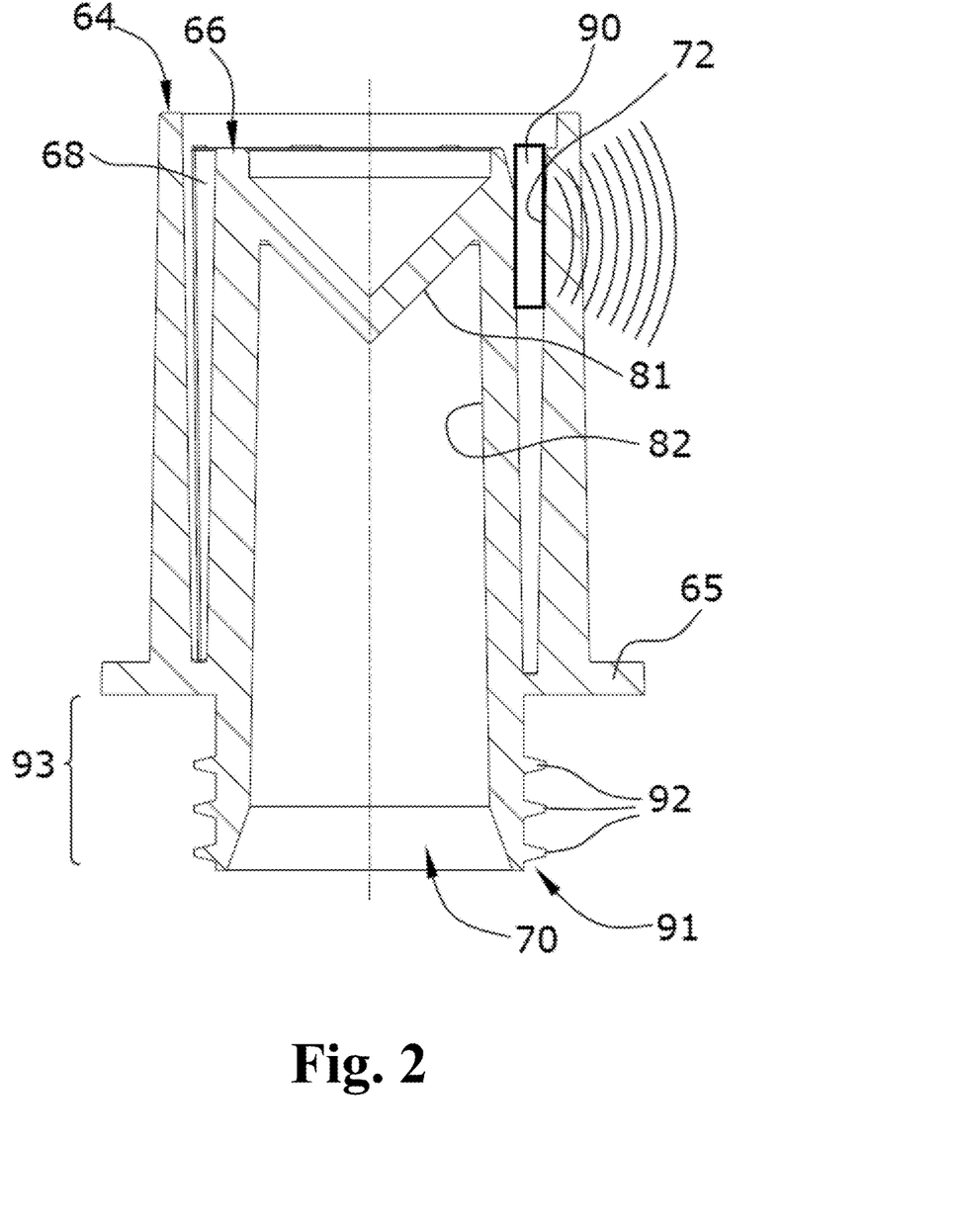
FIG. 2 shows a first second longitudinal cross-section of the vial cap of the vial arrangement of FIG. 1.
Figure 3:
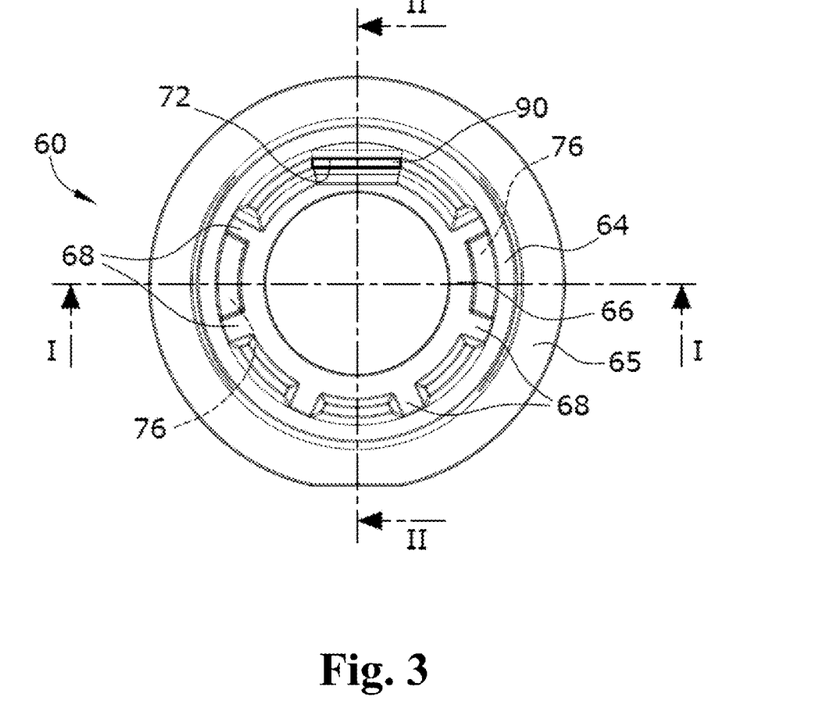
FIG. 3 shows a top view of the vial cap of the vial arrangement of FIG. 1.
Figure 4:
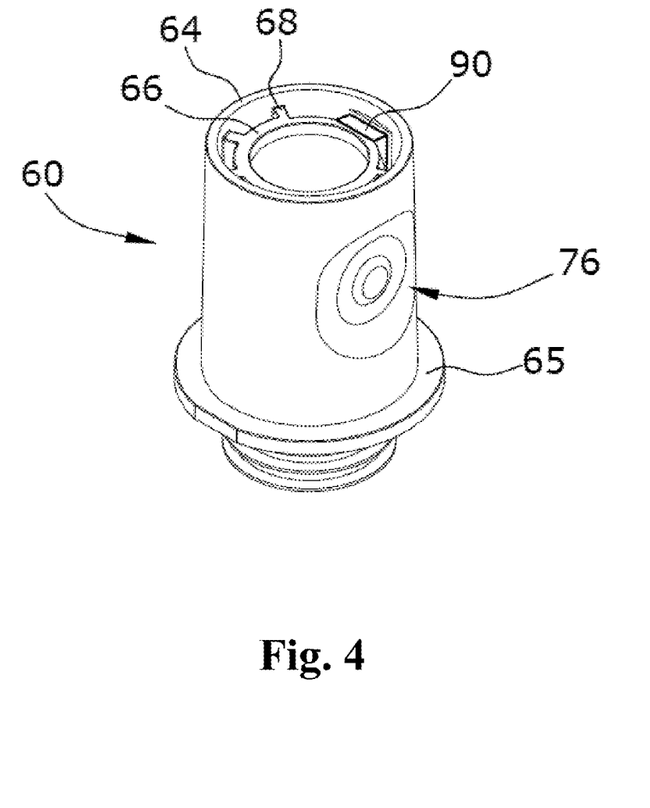
FIG. 4 shows a perspective view of the vial cap of the vial arrangement of FIG. 1.

The outside of the vial cap body 60' is provided with two lateral grip recesses 76 which are arranged opposed to each other. As can be seen in FIGS. 2 to 4, the vial cap 60 is provided with a plane chip cavity 72 which is axially orientated and which houses a RFID chip 90 which is thereby also arranged in an axial plane. Since the RFID chip 90 is arranged in an axial and vertical plane, the antenna of the RFID chip is also arranged in a vertical plane so that the predominant electromagnetic orientation of the RFID antenna is perpendicular to the RFID chip plane and has a radial direction referring to the longitudinal vial axis. The orientation of the chip plane of the RFID chip 90 is symmetrically in the middle with respect to the orientations of the grip planes of the two grip recesses 76.

As shown in FIG. 2, the protruding vial cap portion vertically protruding from the vial 10 is defined by an outer circumferential wall 64 and a coaxial inner circumferential wall 66 which are radially connected to each other by several radial ribs 68. The vial cap body 60' is provided with a circumferential vial cap flange 65 which is axially supported by the radial vial flange 18 of the vial body 14. The vial cap body portion below the vial cap flange 65 defines a substantially cylindrical axial neck portion 93 which projects into the vial interior 26. The axial neck portion 93 is provided with a sealing device 91 which is defined by three sealing lips 92 projecting radially outwardly from the axial neck portion 93. O-rings can also be used.

As shown in FIG. 5, the vial cap 61 according to the second embodiment is provided with a vial cap body 61' defining a different light trap cavity 71 and a different sealing arrangement at the outside of the axial neck portion 95. The axial neck portion 95 is provided with a sealing device 97 being a circular sealing bulge 94 which defines, at the circular boundary line between the ceiling bulge 94 and the inner surface 15 of the vial body 14, an acute angle A of approximately 20°, seen in longitudinal cross-section as shown in FIG. 6.

Figure 6:
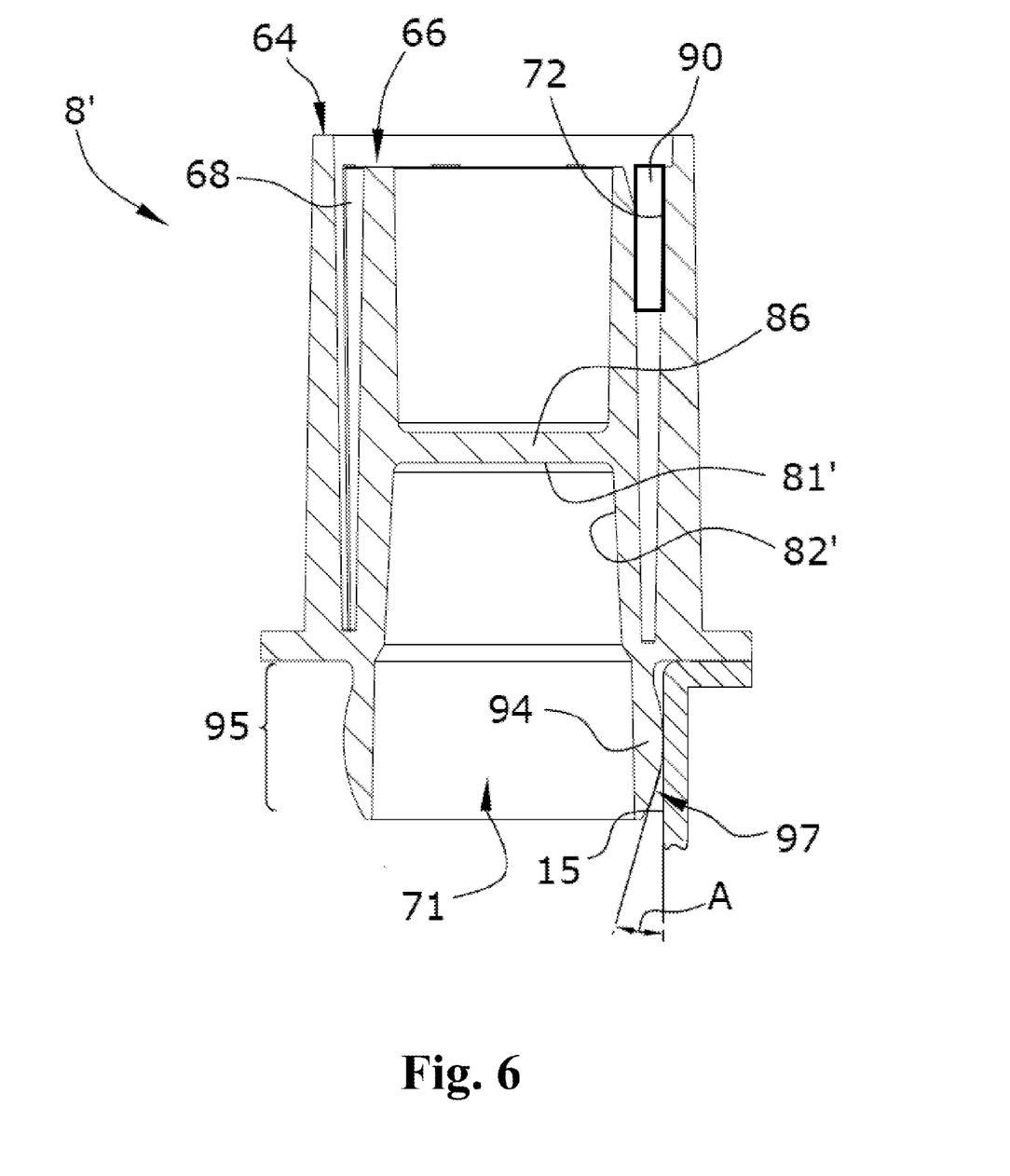
FIG. 6 shows a second longitudinal cross section of the vial cap of the vial arrangement of FIG. 5.
Figure 7:
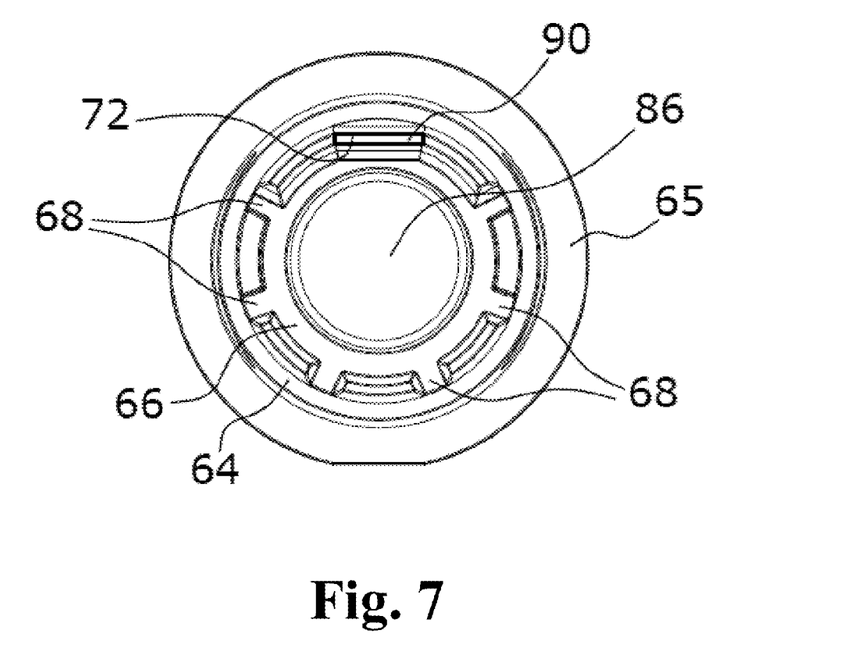
FIG. 7 shows a top view of the vial cap of the vial arrangement of FIG. 5.
Figure 8:
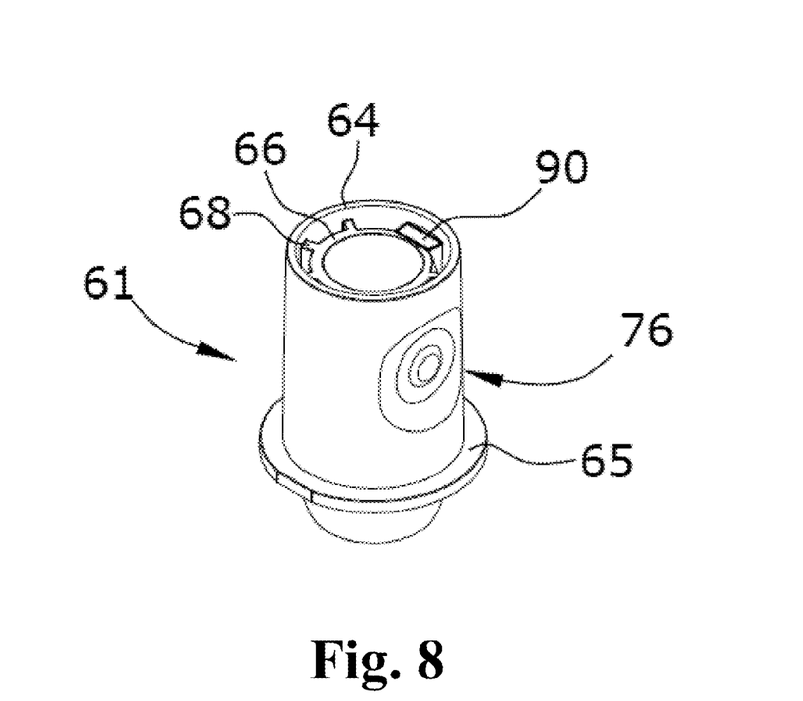
FIG. 8 shows a perspective view of the vial cap of the vial arrangement of FIG. 5.

As shown in FIGS. 5 and 6, the cavity end wall of the light trap cavity 71 is simply a flat end wall 86 lying in a cross (perpendicular) plane with reference to the longitudinal axis of the vial arrangement 8'. The vial arrangement 8' according to this second embodiment is used for turbidity standard solution fluids which completely absorb the intensity of the measurement light beam before the light beam reaches the cavity end wall 86.

The inner surfaces 81, 82; 81', 82' of the vial caps 60, 61 are black-colored and are provided with a light-absorbing surface or structure.

The present invention is not limited to embodiments described herein; reference should be had to the appended claims.

What is claimed is:

1. A nephelometric turbidimeter vial arrangement comprising:
    a vial comprising,
        a transparent cylindrical vial body configured to enclose a vial interior,
        a bottom inlet window, and
        a top vial opening configured to be circular; and
    a separate vial cap comprising a light trap cavity, an outer circumferential wall, an inner circumferential wall, and radial ribs, the outer circumferential wall being connected to the inner circumferential wall via the radial ribs, the separate vial cap being configured to close the top vial opening, the light trap cavity comprising an inner surface which comprises a light absorbing surface, the light trap cavity being configured to be open to the vial interior.

2. The nephelometric turbidimeter vial arrangement as recited in claim 1, wherein the separate vial cap further comprises an axial neck portion which is configured to extend into the vial interior and which defines at least a part of the light trap cavity.

3. The nephelometric turbidimeter vial arrangement as recited in claim 2, wherein the axial neck portion comprises a radial outside part which comprises a circumferential sealing device.

4. The nephelometric turbidimeter vial arrangement as recited in claim 3, wherein the circumferential sealing device is provided as one single circumferential sealing bulge which defines an acute angle of less than 45° with respect to an inner surface of the vial body in a longitudinal cross-section.

5. The nephelometric turbidimeter vial arrangement as recited in claim 1, wherein the light trap cavity further comprises a convex cone arranged at an axial end of the light trap cavity.

6. The nephelometric turbidimeter vial arrangement as recited in claim 1, wherein the separate vial cap further comprises a chip cavity comprising an RFID chip.

7. The nephelometric turbidimeter vial arrangement as recited in claim 6, wherein the chip cavity is arranged in an axial plane so that the plane RFID chip is arranged in the axial plane.

8. The nephelometric turbidimeter vial arrangement as recited in claim 7, wherein the separate vial cap further comprises two lateral grip recesses which are arranged to be opposite to each other.

9. The nephelometric turbidimeter vial arrangement as recited in claim 8, wherein an orientation of the axial plane of the RFID chip is arranged to be in the middle between the orientations of the respective grip planes of the two lateral grip recesses.

10. The nephelometric turbidimeter vial arrangement as recited in claim 1, wherein the separate vial cap further comprises a lateral grip recess.

11. A nephelometric turbidimeter vial cap for a nephelometric turbidimeter vial which comprises a transparent cylindrical vial body configured to enclose a vial interior, a bottom inlet window, and a circular top vial opening, the nephelometric turbidimeter vial cap comprising:
    a light trap cavity,
    an outer circumferential wall,
    an inner circumferential wall, and
    radial ribs,
    wherein,
        the outer circumferential wall is connected to the inner circumferential wall via the radial ribs,
        the nephelometric turbidimeter vial cap is configured to close the circular top vial opening, and
        the light trap cavity comprises an inner surface which comprises a light absorbing surface, the light trap cavity being configured to be open to the vial interior.

12. The nephelometric turbidimeter vial cap as recited in claim 11, further comprising:
    an axial neck portion which is configured to extend into the vial interior and which defines at least a part of the light trap cavity.

13. The nephelometric turbidimeter vial cap as recited in claim 12, wherein the axial neck portion comprises a radial outside part which comprises a circumferential sealing device.

14. The nephelometric turbidimeter vial cap as recited in claim 13, wherein the circumferential sealing device is provided as one single circumferential sealing bulge which defines an acute angle of less than 45° with respect to an inner surface of the vial body in a longitudinal cross-section.

15. The nephelometric turbidimeter vial cap as recited in claim 11, wherein the light trap cavity further comprises a convex cone arranged at an axial end of the light trap cavity.

16. The nephelometric turbidimeter vial cap as recited in claim 11, further comprising a chip cavity comprising an RFID chip.

17. The nephelometric turbidimeter vial cap as recited in claim 11, wherein the chip cavity is arranged in an axial plane so that the plane RFID chip is arranged in the axial plane.

18. The nephelometric turbidimeter vial cap as recited in claim 17, further comprising two lateral grip recesses which are arranged to be opposite to each other.

19. The nephelometric turbidimeter vial cap as recited in claim 18, wherein an orientation of the axial plane of the RFID chip is arranged to be in the middle between the orientations of the respective grip planes of the two lateral grip recesses.

20. The nephelometric turbidimeter vial cap as recited in claim 11, further comprising a lateral grip recess.

\* \* \* \* \*